US00PP14221P39

(12) United States Plant Patent
Malan

(10) Patent No.: US PP14,221 P3
(45) Date of Patent: Oct. 7, 2003

(54) HEMEROCALLIS HYBRID NAMED 'MALJA'

(50) Latin Name: *Hemerocallis hybrid*
Varietal Denomination: Malja

(75) Inventor: Jacques Deetlefs Malan, Rosslyn (ZA)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 09/880,924

(22) Filed: Jun. 15, 2001

(65) Prior Publication Data

US 2002/0194664 P1 Dec. 19, 2002

(51) Int. Cl.[7] ..... A01H 5/00
(52) U.S. Cl. ..... Plt./312

(58) Field of Search ..... Plt./312

(56) References Cited

PUBLICATIONS

GTITM UPOVROM Citation for 'Golden Zebra' as per ZA PBR 01585; Jun. 24, 1994.*
GTITM UPOVROM Citation for 'Golden Zebra' as per QZ PBR 010084; Feb. 15, 2001.*

* cited by examiner

*Primary Examiner*—Kent Bell

(57) ABSTRACT

A new and distinct selection of Hemerocallis hybrid cultivar 'Malja' characterized by its unique combinations of yellow to white and green foliage variegation and golden yellow flowers that are borne on short stems about half the height of the foliage on a plant of short stature.

2 Drawing Sheets

Latin name of the genus and species of the plant claimed: Genus/Species: Hemerocallis hybrid.
Variety denomination: 'Malja'.

BACKGROUND OF THE INVENTION

This invention relates to a new and distinct selection of Hemerocallis hybrid, which is native to Europe, China and Japan, and a member of the Lily family. The new variety, Hemerocallis hybrid cv. 'Malja' resulted from seed which was sown in 1989 in South Africa. These seeds were obtained from a German seed company in 1987 and were labeled "Hemerocallis Miniature Hybrids." The parental cultivars that produced these seeds remained in Germany and were not observed. While the species names of the parental culitvars are unknown, the seeds produced from the parental cultivars characteristically produced plants with a small growth habit. In 1990, a seedling (produced from the above-described seeds) was discovered in South Africa with yellow and green variegation and with dark yellow flowers on short stems. This new selection has been marketed as a perennial landscape plant. 'Malja' can be grown in shade as well as full sun and is slow growing and therefore ideal as a patio or container plant with its unusual variegated foliage.

This new plant has been asexually reproduced by divisions since its discovery in 1990 in South Africa and since 1995 in Azusa, Calif. Through extensive asexual propagation of this plant and observation, it has been established that the plant is true to type, and the novel, exceptional characteristics of this new plant are fixed and stable and reliably passed on to progeny through asexual reproduction.

BRIEF SUMMARY OF THE INVENTION

Hemerocallis hybrid cultivar 'Malja' possesses a vibrant foliage variegation. The foliage in shade is green in the central area of the leaf and white on the margins. In sun conditions, the white leaf color turns to a cream yellow color.

Typically, Hemerocallis plants range in height to two to three feet. The growth habit of 'Malja' remains in the 12" to 15" range. The cultivar 'Malja' typically will bloom for two to three months of the year in South Africa and in Southern California.

DETAILED BOTANICAL DESCRIPTION

Figure 1:
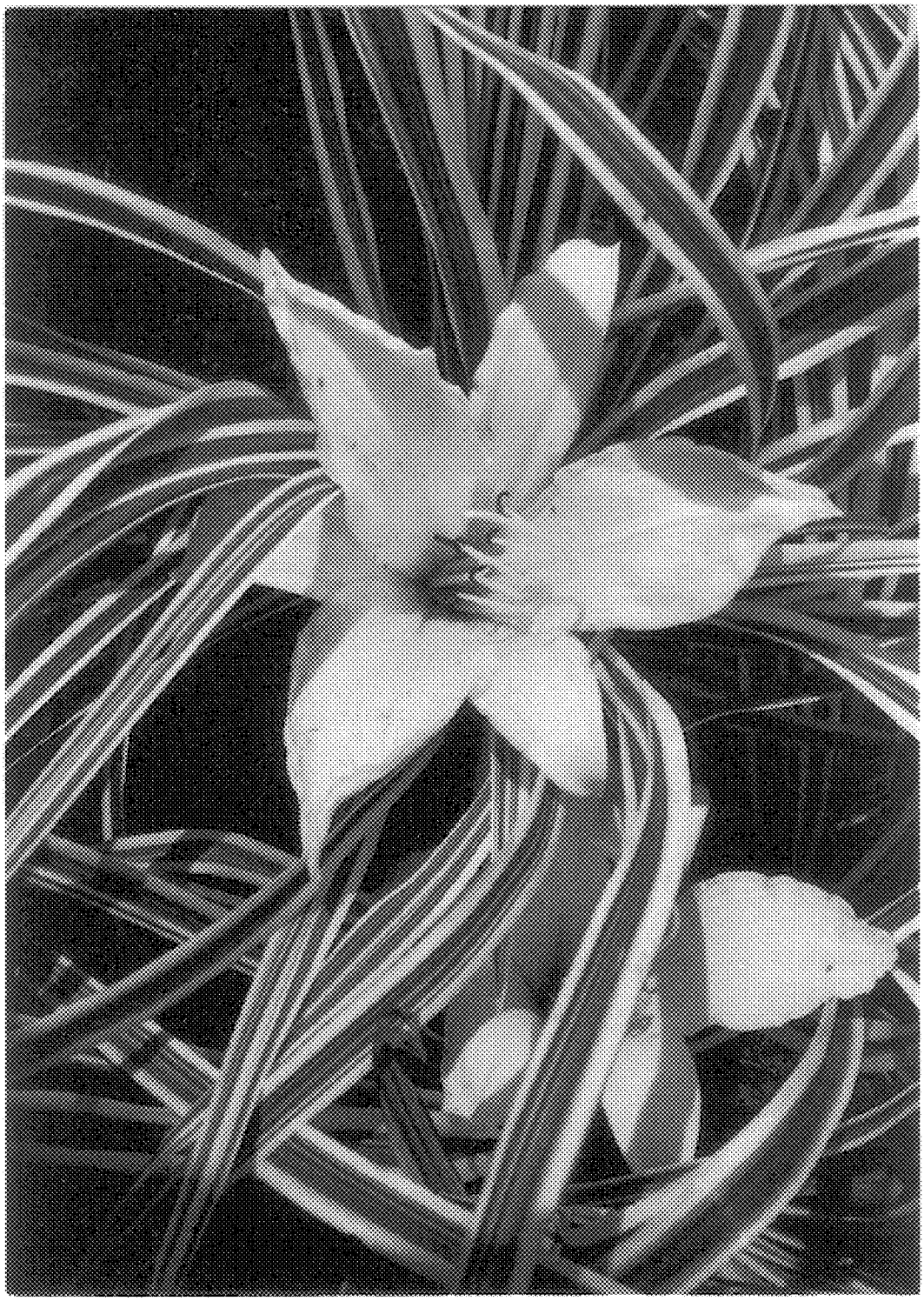
FIG. 1 exhibits a close up of the flower and foliage of cultivar 'Malja'.
Figure 2:
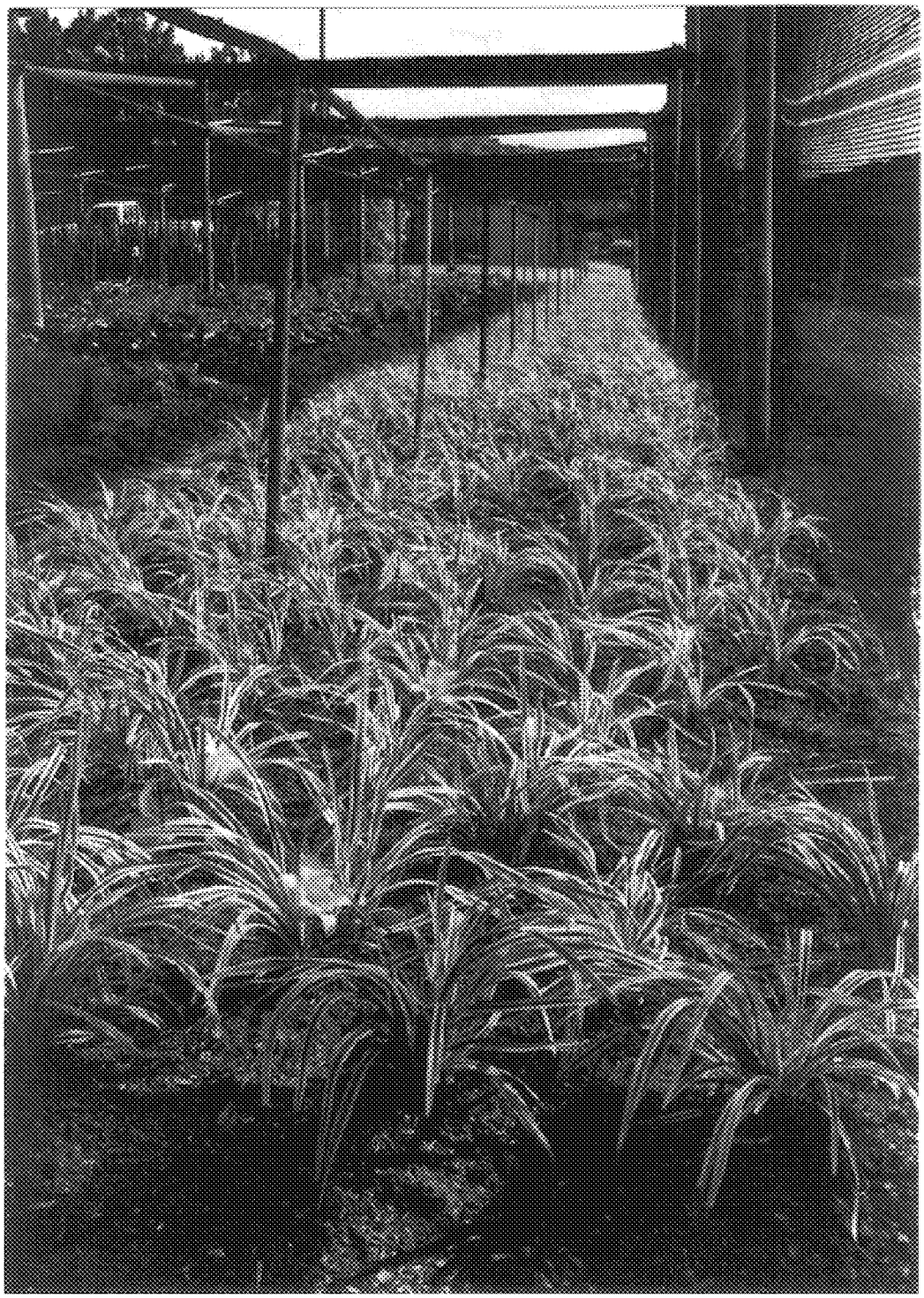
FIG. 2 shows the growth habit and foliage variegation of cultivar 'Malja' and the flowers that appear on short stems within the center of the plant.

Below is a detailed description of Hemerocallis hybrid 'Malja'. Color terminology is from Royal Horticultural Society Colour Charts. It should be noted that growth and/or color varies with time of year, lighting conditions, and soil and nutrient conditions. For example, leaf colors may be brighter green if the plant is grown in soil with greater nitrogen concentrations, and may be more yellow when grown in soil containing lesser amounts of nitrogen.

Measurements are based on plants grown in South Africa and Southern California. The observed plants were approximately eighteen to twenty-four months old. Plants observed in South Africa were field grown, while plants observed in California were container grown.

Overall habit: Herbaceous perennial.
Overall size:
*Maximum height.*—From soil surface to top of foliage ranges from 30 cm to 38 cm.

*Maximum width.*—Of the plant ranges from 30 cm to 45 cm.

*Flowering time in southern California.*—Flowering commences in mid-May and continues until July

*Flowering time in South Africa.*—Flowering commences in mid-November (summer in Southern Hemisphere) and continues until early January.

*Dormancy.*—Winter dormant.

Scapes: About 25 cm in length and about 5 mm in diameter; coloration is alternating longitudinal stripes of Yellow-Green Group 146A and Yellow Group 4C.

Peduncles: Not always present; about 3 cm in length and about 3 mm in diameter; coloration is alternating longitudinal stripes of Yellow-Green Group 146A and Yellow Group 4D.

Pedicles: About 3 to 4 cm in length and about 2 mm in diameter; Yellow-Green Group 146A in color.

Flower:

*Arrangement.*—In clusters of up to 7 on short scapes. Position of flower at time of bloom is approximately half the height of the foliage.

*Type.*—Perianth composed of six similar segments, funnel form to wide — flaring.

*Diameter.*—To 12 centimeters.

*Color.*—Uniform on upper and lower surfaces of tepal Yellow-Orange Group 17B.

*Texture of tepal.*—Slightly fleshy.

*Duration of bloom.*—Flowers ephemeral.

*Tepal margin.*—Smooth and entire, slightly undulating, margins bending inward with age.

*Depth.*—About 6 cm.

*Fragrance.*—None detected.

*Tepal size.*—About 6 to 7 cm long and about 1.5 to 2 cm wide.

*Tepal apex.*—Obtuse to widely acute.

*Flower bud.*—Shape-linear; length 6 to 6½ cm; diameter 1 cm; distinct longitudinal lines that are Yellow-Orange Group 17B in color, alternating with distinct longitudinal lines that are Yellow-Green Group 146C in color. All lines are about 5–6 mm in width.

Reproductive structures:

*Stamens.*—6 in number.

*Anthers.*—Color: Greyed-Orange Group 166A. Length: averaging 4 mm. Width: averaging 1 mm.

*Pollen.*—Color: Yellow-Orange Group 17A. Amount: moderate.

*Filaments.*—Color: Yellow-Orange Group 17B. Length: averaging 2 cm. Width: less than 2 mm.

*Pistil.*—Color: Yellow-Orange Group 17B. Length: averaging 3 cm. Number: one.

*Fruit.*—To date not observed.

Foliage:

*Size.*—Length: ranges from 40 cm–52 cm. Width: ranges from 1.5 cm–2.5 cm.

*Shape.*—Overall: linear, long, strap-like, keeled leaves. Tip: narrow, acuminate tip.

*Margin.*—Entire, slightly to strongly undulate. Color: variegation color varies in sun and shade exposure, typically more yellow is exhibited in full sun conditions and more white is exhibited in shade conditions. Center of leaf is green and margins are variegated. Leaf center color: both upper and lower leaf surfaces are Yellow-Green Group 146A to Yellow-Green Group 147C. Green portion is fairly uniform varying from 5 mm to 10 mm in width and comprising over half the width of the leaf in this color. Leaf margin color: both upper and lower leaf surfaces are Yellow-Group 4C to Yellow Group 7C. The yellow to white variegation exists the length of the entire leaf and on either side of the central green portion of the leaf. The variegation width varies from 5 mm to 10 mm in width. Texture: thin, coriaceus.

Arrangement: Arising from base of the plant.

Pest/disease resistance: Similar to other Hemerocallis plants, susceptible to red spider mites.

Heat/drought tolerance: Prefers temperatures 70° F. to 100° F. with ample soil moisture. Mature plantings tolerate dry soil conditions.

I claim:

1. A new and distinct Hemerocallis plant substantially as herein shown and described.

* * * * *